United States Patent [19]

Or et al.

[11] Patent Number: 5,561,137
[45] Date of Patent: Oct. 1, 1996

[54] THIO-HETEROCYCLIC MACROLACTAM IMMUNOMODULATORS

[75] Inventors: Yat S. Or; Jay R. Luly, both of Libertyville, Ill.

[73] Assignee: Abbott Laboratories, Abbott Park, Ill.

[21] Appl. No.: 212,621

[22] Filed: Mar. 14, 1994

Related U.S. Application Data

[63] Continuation-in-part of Ser. No. 32,958, filed as PCT/US92/07600, Sep. 8, 1992, abandoned, which is a continuation-in-part of Ser. No. 755,208, Sep. 5, 1991, abandoned.

[51] Int. Cl.$^6$ ............... A61K 31/395; C07D 491/16
[52] U.S. Cl. ............... 514/291; 514/411; 540/456
[58] Field of Search ............... 540/436; 514/291, 514/411

[56] References Cited

U.S. PATENT DOCUMENTS

| | | | |
|---|---|---|---|
| 5,247,076 | 9/1993 | Goulet et al. | 540/456 |
| 5,250,678 | 10/1993 | Goulet et al. | 540/456 |
| 5,252,732 | 10/1993 | Sinclair et al. | 540/456 |

FOREIGN PATENT DOCUMENTS

| | | | |
|---|---|---|---|
| 2245891 | 1/1992 | United Kingdom | 540/456 |
| 9304680 | 3/1993 | WIPO | 540/456 |

*Primary Examiner*—Robert T. Bond
*Attorney, Agent, or Firm*—Andreas M. Danckers; Steven R. Crowley

[57] ABSTRACT

Immunomodulatory macrocyclic compounds having the formula:

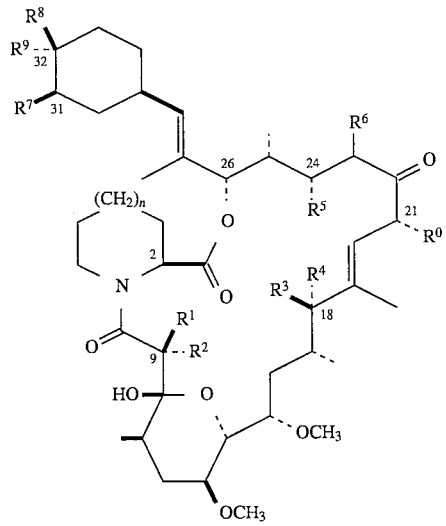

and pharmaceutically acceptable salts, esters, amides and prodrugs thereof, where $R^8$ and $R^9$ are selected such that one of $R^8$ and $R^9$ is hydrogen and the other is $-S(O)_s$-heterocyclic, as well as pharmaceutical compositions containing such compounds and therapeutic methods of their use.

17 Claims, No Drawings

THIO-HETEROCYCLIC MACROLACTAM IMMUNOMODULATORS

This application is a continuation-in-part of U.S. patent application Ser. No. 08/032,958, filed Mar. 17, 1993, now abandoned which is a continuation-in-part of co-pending International Patent Application No. PCT/US92/07600, filed Sep. 8, 1992, which is a continuation-in-part of U.S. patent application Ser. No. 07/755,208, filed Sep. 5, 1991 and now abandoned.

FIELD OF THE INVENTION

The present invention relates to novel chemical compounds having immunomodulatory activity, and in particular to macrolide immunosuppressants. More particularly, the invention relates to semisynthetic analogs of ascomycin and FK-506, to means for their preparation, to pharmaceutical compositions containing such compounds and to methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Undesired side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et at., in European Patent Application No. 184162, published Jun. 11, 1986, disclose a number of macrocyclic compounds isolated from the genus Streptomyces. Immunosuppressant FK-506, isolated from a strain of S. tsukubaensis, is a 23-membered macrocyclic lactone represented by formula 1 a, below. Other related natural products, such as FR-900520 (1 b) and FR-900523 (1c), which differ from FK-506 in their alkyl substituent at C-21, have been isolated from S. hygroscopicus yakushimnaensis. Yet another analog, FR-900525, produced by S. tsukubaensis, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323865, published Jul. 12, 1989.

Although the immunosuppressive activity of FK-506 has been clinically confirmed, its toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

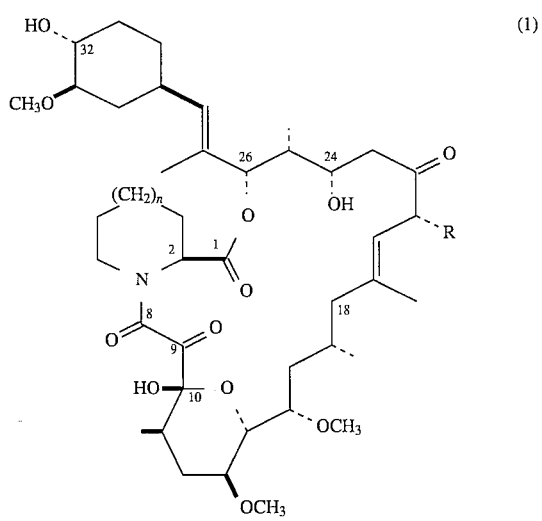

| | |
|---|---|
| 1(a): FK-506 | R = $CH_2CH=CH_2$; n = 1 |
| 1(b): FR-900520 | R = $CH_2CH_3$; n = 1 |
| 1(c): FR-900523 | R = $CH_3$; n = 1 |
| 1(d): FR-900525 | R = $CH_2CH=CH_2$; n = 0 |

Fermentation products of FK-type compounds include C-21 -epi derivatives of FK-506; a 31 -demethylated derivative of FK-506; 31 -oxo-FK-506; and compounds derived from FK-506, FR-900523 and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published derivatives include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bis-demethylated 13,31-dihydroxy ring-rearranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether and aryl ether formation at C-32 and/or C-24, oxidation of C-32 alcohol to the ketone, and epoxide formation at C-9.

Although some of these modified compounds exhibit immunosuppressive activity, the need remains for macrocyclic immunosuppressants which do not have the serious side effects frequently associated with immunosuppressant therapy. Accordingly, one object of the invention is to provide novel semisynthetic macrolides which possess the desired immunomodulatory activity but which minimize undesired side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, one of the above compounds. Yet another object of the invention is to provide a method of treating a variety of disease states, including post-transplant tissue rejection and autoimmune disfunction.

SUMMARY OF THE INVENTION

In one aspect of the present invention are disclosed compounds of the formula:

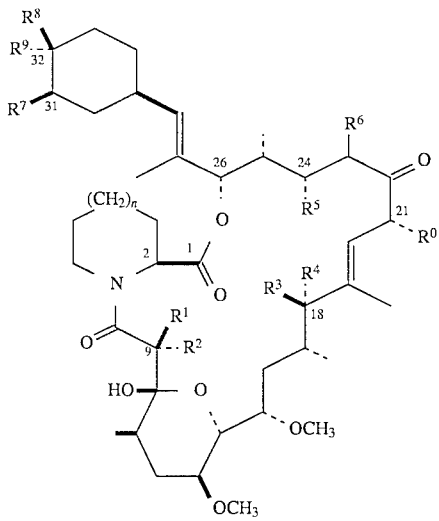

and pharmaceutically acceptable salts, esters, amides and prodrugs thereof, wherein n, $R^0$, $R^1$, $R^2$, $R^3$, $R^4$, $R^5$, $R^6$, $R^7$, $R^8$ and $R^9$ are specifically defined, which possess immunosuppressive, antimicrobial, antifungal, antiviral, antiinflammatory and antiproliferative activity, as well as the ability to reverse chemotherapeutic drug resistance. Other aspects of the present invention include pharmaceutical compositions comprising the above compounds in combination with a pharmaceutically acceptable carrier; processes for the preparation of these compounds; synthetic intermediates useful in the preparations of these and other immunomodulator derivatives of ascomycin; and methods of immunomodulatory treatment of a human or veterinary patients in need of such treatment by the administration of a therapeutically effective amount of a novel compound according to the present invention.

DETAILED DESCRIPTION OF THE INVENTION

The compounds of the present invention are those described by the general formula:

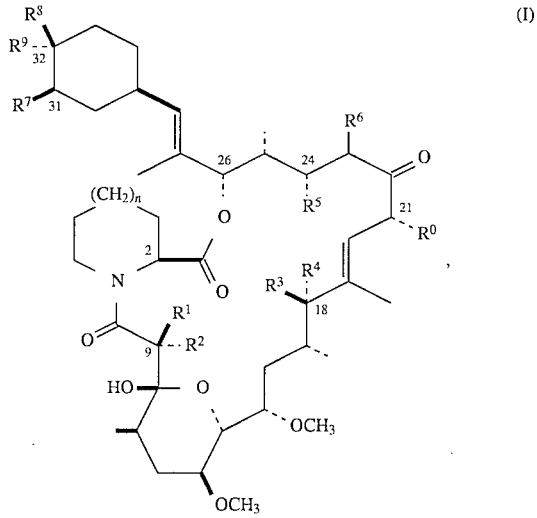

as well as the pharmaceutically acceptable salts, esters, amides and prodrugs thereof, wherein:

n is zero or one;

$R^0$ is hydrogen, methyl, ethyl, allyl, propyl, 2-hydroxyethyl, cyclopropylmethyl, 2-oxopropyl or 2-ethanal;

$R^1$ and R2 are independently hydrogen or hydroxy, subject to the proviso that when one of $R^1$ or $R^2$ is hydroxy, the other of $R^1$ and $R^2$ is hydrogen; or, alternatively, $R^1$ and $R^2$ taken together are oxo;

$R^3$ and $R^4$ are independently hydrogen, halogen, or hydroxy, subject to the proviso that when one of $R^3$ or $R^4$ is halogen or hydroxy, the other of $R^3$ and $R^4$ is hydrogen; or, alternatively, $R^3$ and $R^4$ taken together are oxo;

$R^5$ is hydrogen, hydroxy, or protected hydroxy, and $R^6$ is hydrogen; or alternatively, $R^5$ and $R^6$ taken together form a C-23/C-24 bond;

$R^7$ is hydroxy, methoxy or protected hydroxy, where protected hydroxy is as defined below; and $R^8$ and $R^9$ are selected such that one of $R^8$ and $R^9$ is hydrogen, and the other is —S(O)$_s$—Het, where s is zero, one or two, and Het is defined below.

Preferred among the compounds of the present invention are those in which the integer n is one; R is ethyl, allyl or propyl; $R^1$ and $R^2$, taken together, are oxo; $R^3$ and $R^4$ are hydrogen or hydroxy; $R^5$ is hydrogen or hydroxy; $R^7$ is methoxy; and/or $R^8$ is —S(O)$_s$—Het. Especially preferred among these compounds are those in which $R^5$ is hydroxy, as are those in which Het is selected from pyrrolyl, pyrazolyl, imidazolyl, pyridyl, pyrazinyl, pyrimidinyl, indolyl, triazolyl and tetrazolyl.

Representative of some of the preferred compounds of the invention are those having the formula:

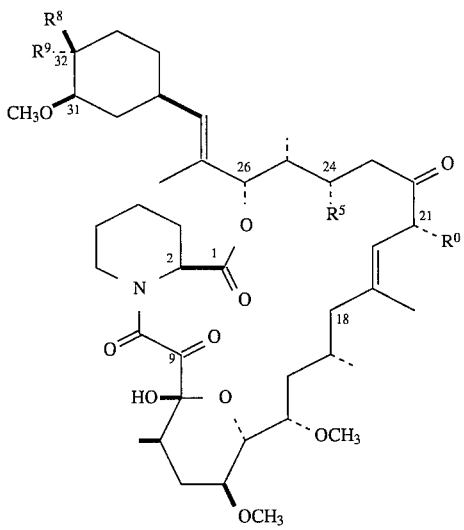

(II)

where $R^0$, $R^5$, $R^8$ and $R^9$ are as previously defined. Of these, particularly preferred compounds are those in which $R^0$ is ethyl, allyl or propyl; $R^5$ is selected from the group consisting of hydrogen and hydroxy; and/or $R^8$ is $—S(O)_s—$Het. Again, those compounds in which $R^5$ is hydroxy are especially preferred, as well as those in which Het is selected from pyrrolyl, pyrazolyl, imidazolyl, pyridyl, pyrazinyl, pyrimidinyl, indolyl, triazolyl and tetrazolyl.

When examined for immunomodulatory activity using a common in vitro biological assay, the compounds of the invention are seen to be potent immunosuppressive agents. Consequently, it is expected that the compounds will possess immunosuppressive, antimicrobial, antifungal, antiviral, antiinflammatory and antiproliferative activity. Moreover, the compounds of the invention would be expected to possess the ability to reverse chemotherapeutic drug resistance. As agents which block T-cell activation, a prerequisite for HIV proliferation, the compounds may be useful as prophylactics for the prevention of HIV replication. While, the compounds of the invention would be useful when used independently of other agents, combination therapy with other immunosuppressants would be expected to be beneficial as well. These other agents include but are not limited to FK-506, rapamycin, cyclosporin A, mycophenolic acid, azathioprine, prednisolone, cyclophosphamide, brequinar and leflunomide.

As used throughout this Specification and Claims, the following terms have the meanings specified:

The term "aryl" as used herein refers to mono-, di-, tri- or tetracyclic aromatic radicals, the rings of which are each comprised of from 3 to 7 carbon atoms, including but not limited to phenyl, 1- or 2-naphthyl, fluorenyl, (1,2)-dihydronaphthyl, (1,2,3,4)-tetrahydronaphthyl and indenyl. Such aryl radicals may optionally be substituted with one, two or three substituents independently selected from halogen, hydroxy, —CN, —CHO, —COOH, —NO$_2$, —N$_3$, —(C1–C7-alkyl), —(C2–C6-alkenyl), —(C2-to-C6-alkynyl), mono-, di-, tri-, or perhalogenated —(C–C$_6$-alkyl), —(CH$_2$)$_m$N(C1–C6-alkyl)$_2$, where m is zero to six, —S(O)$_s$(C1–C6-alkyl) where s is zero to two, —C(O)NH–(C1–C6-alkyl), —C1–C6-alkoxy, —(CH$_2$)$_m$O(C1–C6-alkyl), —(CH$_2$)$_m$OC(O)(C1–C6-alkyl), —(CH$_2$)$_m$C(O)O(C1–C6-alkyl), —S(O)$_2$N(C1–C6-alkyl)$_2$, —C≡C-Si(CH$_3$)$_3$, —OC(O)(C1–C6-alkyl), guanidino, unsubstituted aryl, and unsubstituted Het; or, taken together, any two adjacent compatible substituents in a di- or trisubstituted aryl group form a 5-, 6- or 7-membered carbocyclic ring or a 5-, 6- or 7-membered heterocyclic ring wherein the ring atoms consist of carbon atoms and zero, one or two heteroatoms independently selected from the group consisting of -0-, —S(O)$_s$—and —N(C1-C6-alkyl)-.

The term "alkenyl" as used herein refers to a monovalent straight or branched chain radical of 2 to 10 (unless specified otherwise) carbon atoms containing at least one carbon—carbon double bond including, but not limited to ethenyl, 1-propenyl, 2-propenyl, 2-methyl1-propenyl, 1-butenyl and 2-butenyl.

The term "alkoxy" as used herein refers to an oxygen radical to which has been appended an alkyl radical, as defined below.

The term "alkyl" as used herein refers to a monovalent straight chain or branched chain radical of 1 to 10 (unless specified otherwise) carbon atoms including, but not limited to, methyl, ethyl, n-propyl, isopropyl, n-butyl, sec-butyl, isobutyl, tert-butyl, hexyl and decyl.

The term "alkynyl" as used herein refers to a monovalent straight or branched chain radical of 3 to 10 (unless specified otherwise) carbon atoms containing at least one carbon—carbon triple bond including, but not limited to ethynyl, butynyl and pentynyl.

The term "cyclo(alkyl)" as used herein refers to a monovalent cyclic radical of 3 to 10 (unless specified otherwise) carbon atoms including, but not limited to, cyclopropyl, cyclobutyl, cyclopentyl and cyclohexyl.

The term "Het" as used herein refers to any aromatic 5-, 6- or 7-membered monocyclic ring or a bi- or tri-cyclic radical comprising fused five- or six-membered rings having ring carbon atoms and between one and three heteroatoms independently selected from oxygen, sulfur and nitrogen, wherein (i) each 5-membered ring has 2 double bonds and each 6- or 7-membered ring has 3 double bonds, (ii) the nitrogen and sulfur heteroatoms as well as the carbon atoms may optionally be oxidized, (iii) the nitrogen heteroatom may optionally be quaternized, (iv) any of these rings may be fused to a benzene ring, and (v) any carbon or heteroatom with suitable valence may bear a substituent independently selected at each occurrence from the group consisting of halogen, hydroxy, —COOH, —CN, —CHO, —NO$_2$, —N$_3$, —(C1–C6-alkyl), —(C2–C6-alkenyl), —(C2–C6-alkynyl), mono-, di-, tri-, or perhalogenated —C1–C6-alkyl, —(CH$_2$)$_m$N(C1–C6-alkyl)$_2$ where m is zero to six, —S(O)$_s$(C1–C6-alkyl) where s is zero to two, —C(O)NH(C1–C6-alkyl), —(CH$_2$)$_m$O(C1–C6-alkyl), —(CH$_2$)$_m$OC(O)(C1–C6-alkyl), —(CH$_2$)$_m$C(O)O(C1–C6-alkyl), —S(O)$_2$N(C1–C6-alkyl)$_2$, —C≡C—Si(CH$_3$)$_3$, —C1–C6-alkoxy, —OC(O)(C1–C6-alkyl), guanidino, unsubstituted aryl, and unsubstituted Het; or, taken together, any two adjacent compatible substituents in a di-, tri-. tetra- or pentasubstituted Het group form a 5-, 6- or 7-membered carbocyclic ring or a 5-, 6- or 7-membered heterocyclic ring wherein the ring atoms consist of carbon atoms and zero, one or two heteroatoms independently selected from the group consisting of—O—, —S(O)$_s$— where s is as defined above, and —N(C1–C6-alkyl)-. Het groups include, but are not limited to, pyrrolyl, pyrazolyl, cytosinyl, thiocytosinyl, imidazolyl, pyridyl, pyrazinyl, pyrimidinyl, pyridazinyl, xanthenyl, xanthonyl, xanthopterinyl, oxazoyl, thiouracilyl, isoxazolyl, indolyl, quinolinyl, uracilyl, urazolyl, uricyl, triazolyl, tetrazolyl, thiazolyl, isothiazolyl, isoquinolinyl, thyminyl, benzimidazolyl, benzothiazolyl, benzoxazolyl, furyl, thienyl and benzothienyl.

The term "hydroxy-protecting group" as used herein refers to those radicals which are known in the art of organic synthesis (T. W. Greene and P. G. M. Wuts, Protective Groups in Organic Synthesis, 2nd ed., John Wiley & Son, Inc., 1991) to protect a hydroxyl group against undesirable reaction during synthetic procedures and to be selectively removable. Examples include, but are not limited to, methylthiomethyl, dimethylthexylsilyl, trisubstituted silyl such as tris(loweralkyl)silyl (e.g., trimethylsilyl, triethylsilyl, tributylsilyl, tri-isopropylsilyl, tert-butyldimethylsilyl, tri-tert-butylsilyl, triphenylsilyl, triphenylmethyldimethylsilyl, etc.); loweralkyldiarylsilyl (e.g., methyldiphenylsilyl, ethyldiphenylsilyl, propyldiphenylsilyl, tert-butyldiphenylsilyl, etc.); triarylsilyl (e.g., triphenylsilyl, trixylylsilyl, etc.); triarylalkylsilyl (e.g., tribenzylsilyl, etc.); alkylacyl (e.g., acetyl); aryloyl (e.g., benzoyl); alkoxycarbonyl (e.g., ethoxycarbonyl); —$S(O)_2$—(loweralkyl); —$S(O)_2$—(aryl); acyl substituted with an aromatic group and the like.

The term "oxo" as used herein refers to an oxygen atom forming a carbonyl group.

The term "protected hydroxy" as used herein refers to a hydroxy group to which has been attached a hydroxy-protecting group, as defined above.

"Pharmaceutically acceptable salts, esters, amides and prodrugs" refers to those carboxylate salts, amino acid addition salts, esters, amides and prodrugs of the compounds of the present invention which are, within the scope of sound medical judgment, suitable for use in contact with the tissues of humans and lower animals without undue toxicity, irritation, allergic response, or the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention, which may be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylarmnonium, methylamine, dimethylamine, trimethylamine, triethylamine, ethylamine, and the like (see, for example S. M. Berge, et al., "Pharmaceutical Salts," *J. Pharm. Sci.*, 66:1–19 (1977)).

Examples of pharmaceutically-acceptable, non-toxic esters of the compounds of this invention include C1-to-C6-alkyl esters wherein the alkyl group is a straight or branched chain. Acceptable esters also include C5-to-C7-cycloalkyl esters as well as arylalkyl esters such as, but not limited to benzyl. C1-to-C4 alkyl esters are preferred. Esters of the compounds of the present invention may be prepared according to conventional methods. Conversely, non-toxic esters of alcoholic moieties on the compounds of the invention may be constructed by condensing these alcohols with C1-to-C6-alkyl carboxylic acids, C1-to-C6-alkyl dicarboxylic acids or aryl-carboxylic acids. Examples of such esters include, but are not limited to acetyl, benzoyl or hemisuccinyl.

Examples of pharmaceutically-acceptable, non-toxic amides of the compounds of this invention include amides derived from ammonia, primary C1-to-C6-alkyl amines and secondary di-C1-to-C6-alkyl amines. In the case of secondary amines the amine may also be in the form of a 5-or- 6 membered heterocycle containing one nitrogen atom. Amides derived from ammonia, C1-to-C3-alkyl primary amides and di-C1-to-C2-alkyl secondary amides are preferred. Amides of the compounds of the invention may be prepared according to conventional methods.

"Prodrug" refers to compounds that are rapidly transformed in vivo to yield the parent compound of the above formula, for example, by hydrolysis in blood. A thorough discussion is provided in T. Higuchi and V. Stella, "Prodrugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987.

Prodrugs of compounds of the present invention may be prepared by suitable methods. For those compounds in which the prodrug moiety is an amino acid or peptide functionality, the condensation of the drug's amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z or Cbz), o-chlorobenzyloxycarbonyl ((2-C1)Z)), p-nitrobenzyloxycarbonyl (Z($NO_2$)), p-methoxybenzyloxycarbonyl (Z(OMe)), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt), dimethylphosphino-thioyl (Mpt), and the like.

The examples for protecting groups for carboxyl groups involve, for example, benzyl ester (OBzl), cyclohexyl ester, 4-nitrobenzyl ester (OBzl$NO_2$), t-butyl ester (OtBu), 4-pyridylmethyl ester (OPic), and the like.

In the course of the synthesis of certain of the compounds of the present invention, specific amino acids having functional groups other than amino and carboxyl groups in the branched chain such as arginine, cysteine, serine and the like may be protected, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2, 6-dimethyl-benzenesulfonyl (Mts) and the like; the thiol group in cysteine may be protected with benzyl, p-methoxybenzyl, triphenyhnethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP), and the like.

Numerous asymmetric centers exist in the compounds of the present invention. Except where otherwise noted, the present invention contemplates the various stereoisomers and mixtures thereof. Also, it is understood that when a variable, such as the subscript m or s in the definition of Het, occurs more than once in a formula, its value is chosen independently at each occurrence.

The potent immunomodulatory activity which compounds of the instant invention demonstrate, in common in vitro biological assays, indicate that these compounds possess immunosuppressive, antimicrobial, antifungal, antiviral, antiinflammatory, and antiproliferative activity, and possess the ability to reverse chemotherapeutic drug resistance. As agents which block T-cell activation, a prerequisite for HIV proliferation, the compounds are useful as prophylactics for the prevention of HIV replication. While the compounds of the invention would be useful when used alone, combination therapy with other immunosuppressants, such as, FK506, rapamycin, cyclosporin A, picibanil, mycophenolic acid, azathioprine, prednisolone, cyclophosphamide, brequinar and leflunomide, would also be expected to be beneficial.

As immunosuppressants, the compounds of the present invention are useful when administered for the prevention immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the compounds of the invention would also find utility in the treatment of autoimmune diseases, such as rheumatoid arthritis, systemic lupus erythematosus, Hashimoto's thyroiditis, multiple sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis would suppress the replication of the virus, since the virus relies upon the host T-cell's proliferative functions to replicate.

Further uses include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidennolysis bullosa, urticaria, angioedemas, vasculitides, erythemas, cutaneous eosinophilias, Lupus erythematosus, ache and Alopecia areata; various eye diseases (autoimmune and otherwise) such as keratoconjunctivitis, vernal conjunctivitis, keratitis, herpetic keratitis, conical cornea, dystrophia epithelialis comeae, corneal leukoma, ocular pemphigus, Mooren's ulcer, Scleritis, Graves' opthalmopathy, Vogt-Koyanagi-Harada syndrome, sarcoidosis, etc.; reversible obstructive airway disease, which includes conditions such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds of the invention.

Other treatable conditions would include but are not limited to ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; puhnonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmentation of chemotherapeutic effect, preventing or treating activity of cytomegalovirus infection, particularly HCMV infection, anti-inflammatory activity, and so on.

Additionally, some compounds also possess FK-506 antagonistic properties, and are thus useful in the treatment of immunodepression or a disorder involving immunodepression. Examples of disorders involving immunodepression include AIDS, cancer, senile dementia, trauma (including wound healing, surgery and shock), chronic bacterial infection, and certain central nervous system disorders. The immunodepression to be treated may be caused by an overdose of an immunosuppressive macrocyclic compound, for example derivatives of 12-( 2-cyclohexyl-1-methylvinyl)-13, 19,21,27-tetramethyl-11,28-dioxa-4-azatricyclo [22.3.1.0 $^{4,9}$]octacos-18-ene such as FK-506, or rapamycin. Overdosing of such medicants by patients is quite common upon their realizing that they have forgotten to take their medication at the prescribed time and can lead to serious side effects.

A further situation in which the compounds of the present invention may be used to treat immunosuppression is in vaccination. It is sometimes found that the antigen introduced into the body for the acquisition of immunity from disease also acts as an immunosuppressive agent, and therefore antibodies are not produced by the body and immunity is not acquired. By introducing a compound of the present invention into the body (as in a vaccine), the undesired immunosuppression may be overcome and immunity acquired.

The compounds of the present invention may also find utility in the chemosensitization of drug resistant target cells. Cyclosporin A and FK-506 are known to be effective modulators of P-glycoprotein, a substance which binds to and inhibits the action of anticancer drugs; by inhibiting P-glycoprotein, they are capable of increasing the sensitivity of multidrug resistant (MDR) cells to chemotherapeutic agents. It is believed that the compounds of the invention may likewise be effective at overcoming resistance expressed to clinically useful antitumour drugs such as 5-fluorouracil, cisplatin, methotrexate, vincristine, vinblastine and adriamycin, colchicine and vincristine.

Further, it has recently been shown that the steroid receptor-associated heat shock proteins, hsp56 or hsp59, belong to the FK506 family of immunophilin proteins. The ability of asteroid receptor-associated heat shock protein to bind the immunosuppressive macrolide FK506 may suggest that the steroid receptor and immunophilin signal transduction pathways are functionally interrelated. The combined treatment of compounds of the present invention and low concentrations of asteroid ligand (eg. progesterone, dexamethasone) may result in a significant enhancement of target gene expression over that seen in response to ligand alone. Thus, the compounds of the present invention may potentiate steroid-mediated transactivation.

Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation.

Accordingly the pharmaceutical compositions of the present invention are those which comprise a therapeutically effective amount of a compound of the invention in combination a pharmaceutically acceptable carrier. Particular compositions are those which are useful for treating a patient for immune-mediated organ or tissue allograft rejection, a graft-versus-host disease, an autoimmune disease, a reversible obstructive airway disease, a hyperproliferative disease, or an ischemic or inflammatory intestinal or bowel disease.

Likewise, the methods of the present invention comprising treating a patient in need of immunosuppressive, anti-inflammatory, antimicrobial, antifungal, antiviral or antiproliferative therapy, or requiring the reversal of chemotherapeutic drug resistance, by administering a therapeutically effective amount of a compound of the invention for such time and in such amounts as is necessary to produce the desired result.

When used in the above or other treatments, by "therapeutically effective amount" of one of the compounds of the present invention is meant a sufficient amount of the compound to treat a particular disorder, at a reasonable benefit/risk ratio. The compounds of the invention may be employed in pure form or, where such forms exist, in pharmaceutically acceptable salt, ester or prodrug Ibrm. Alternatively, the compound may be administered as pharmaceutical compositions containing the compound of interest in combination with one or more pharmaceutically-acceptable excipients. It will be understood, however, that the total daily usage of the compounds and compositions of the present invention will be decided by the attending physician within the scope of sound medical judgment.

The specific therapeutically-effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.001 to about 10 mg/kg of patients body mass/day. For purposes of oral administration, more preferable doses may be in the range of from about 0.005 to about 3 mg/kg/day. If desired, the effective daily dose may be divided into multiple doses for purposes of administration; consequently, single dose compositions may contain such amounts or submultiples thereof to make up the daily dose.

In the pharmaceutical compositions of the present invention, a compound of the invention is combined with a pharmaceutically acceptable carrier or excipient, meaning a non-toxic solid, semi-solid or liquid filler, diluent, encapsulating material or formulation auxiliary of any type. The compositions may be administered orally, rectally, parenterally, intracisternally, intravagmally, intraperitoneally, topically (as by powders, ointments, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable fomulations may be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically-acceptable excipient or carrier, such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions may contain, in addition to the active compounds, suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye, as for the treatment of immunemediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the invention may be prepared using one or more processes. The starting materials for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, *Novel immunosuppressants isolated from A streptomyces. I. Taxonomy of the producing strain. J. Antibiot.,* 1988. XLI(11), 1586–1591; (ii) H. Hatanaka, T. Kino, S. Miyata, N. Inamura, A. Kuroda, T. Goto, H. Tanaka and M. Okuhara, FR-900520 and FR-900523, *Novel immunosuppressants isolated from A streptomyces. II. Fermentation, isolation and physico-chemical and biological characteristics. J. Antibiot.,* 1988. XLI (11), 1592–1601; (iii) T. Arai, Y. Koyama, T. Suenaga and H. Honda, *Ascomycin, An Antifungal Antibiotic. J. Antibiot.,* 1962. 15(231–2); and (iv) T. Arai in U.S. Pat. No. 3,244,592. One or more of the processes discussed below may then be employed to produce the desired compounds of the invention.

Such processes comprise:

(a) producing a compound of formula II, which contains a CH—$OSO_2F$ or CH—$OSOCF_3$ group, by selective activation of a CH—OH group with an appropriate amount of fluorosulfonic anhydride or trifluoromethanesulfonic anhydride under conditions suitable for the production of the desired product;

(b) producing a compound of formula II, which contains a CH—OH group with inverted stereochemistry, by first activate a selected CH—OH group to its corresponding sulfonate, examples are but not limited to CH—$OSO_2F$ and CH—$OSO_2CF_3$ and reacting with dimethylsulfoxide-water, or water with other cosolvents.

(c) producing a compound of formula II, which contains a CH—S—Het group by reacting with a corresponding HS—Het and a compound of formula II containing a CH—$OSO_2F$ or CH—$SO_2CF_3$ group.

(d) producing a compound of formula II, which contains a CH—$S(O)_s$—Het group by oxidation of a compound of formula II containing a CH—S—Het group.

In process (a), a suitable reagent for activation of an alcohol of formula II is sulfonyl chlorides, fluorosulfonyl anhydride (prepared according to the procedure described by S. Kongpricha, W. G. Preusse and R. Schwarer, in Inorganic Synthesis, 1968, 11, p151–155) or trifluoromethanesulfonyl anhydride (Aldrich). The activation may be carried out in a solvent which does not adversely affect the reaction (e.g. diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from −100° to 30° C., and more preferably from −78° to 0°C. The reaction may require 20 minutes to 24 hours to complete, depending on the reagent chosen.

In process (b), a suitable reagent for activation of an alcohol of formula II is sulfonyl chlorides, fluorosulfonyl anhydride or trifluoromethanesulfonyl anhydride (Aldrich). The activation may be carried out in a solvent which does not adversely affect the reaction (e.g. diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, luffdine, picoline, quinoline, diisopropylethylamine and the like. The reaction temperature is preferably from −100° to 30° C., and more preferably from −78° to 0° C. The reaction may require 20 minutes to 24 hours to complete, depending on the reagent chosen.

A suitable reagent for the inversion of stereochemistry is water, dimethylsulfoxide, pyridine N-oxide, dimethylphosphite or triphenylphosphine oxide. The inversion reaction may be carried out in a solvent which does not adversely affect the reaction (e.g. dioxane, tetrahydrofuran, dimethylsulfoxide or a mixture thereof. The reaction may require cooling or heating, depending on the method used. The reaction temperature is preferably from −100° to 30° C., and more preferably from −78° to 0° C. The reaction may require 20 minutes to 24 hours to complete, depending on the reagent chosen.

In process (c), a suitable reagent is HS—Het. The activation may be carried out in a solvent which does not adversely affect the reaction (e.g. diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, luffdine, picoline, quinoline, diisopropylethylamine and the like. The reaction temperature is preferably from −100° to 30° C., and more preferably from −78° to 0° C. The reaction may require 20 minutes to 24 hours to complete, depending on the reagent chosen.

In process (d), a suitable oxidizing reagent is organic or inorganic peracids, peroxides, ruthenium tetraoxide, chromates, permanganates or periodates. The oxidation may be carried out in a solvent which does not adversely affect the reaction (e.g. diethyl ether, dichloromethane, tetrahydrofuran, chloroform or a mixture thereof). The reaction may require cooling or heating, depending on the method used. Further, the reaction is preferably conducted in the presence of an inorganic base such as cesium bicarbonate, cesium carbonate, potassium carbonate and the like. The reaction temperature is preferably from −100° to 30° C., and more preferably from −78° to 0° C. The reaction may require 20 minutes to 24 hours to complete, depending on the reagent chosen.

The present invention can be illustrated by the following non-limiting, representative examples.

EXAMPLE 1 a

Formula II: $R^8$=H; $R^9$=—OSO$_2$F 2,6-lutidine (0.89mL) was added into a stirred solution of ascomycin (3.0 g) in freshly distilled (from calcium hydride) dichloromethane (30 mL) at −78° C. Fluorosulfonyl anhydride (0.49 mL) in dichloromethane (10 mL) was added dropwise into the reaction mixture at −78° C. After being stirred for 1 hour, the reaction mixture was partitioned between ice-cold ether and 0.15 N hydrochloric acid. The organic phase was washed once with ice-cold brine and dried over magnesium sulfate. The filtrate was poured on a silica gel column (50 g) prepacked in ether and eluted with ether. Solvent was removed in vacuo to give the title compound as light pink solid. Yield: 3.4 g; MS (FAB) m/e M+K=912.

EXAMPLE 1b

Formula II; $R^8$=—OH; $R^9$=H

The title compound of Example 1 a (3.4 g) was dissolved in dimethylsulfoxide (25 mL) and stirred at room temperature for 2 hours. The reaction was partitioned between ethyl acetate and sodium bicarbonate. The organic phase was washed once with brine, dried over magnesium sulfate and solvent removed in vacuo. The crude product was purified by silica gel chromatography (90 g) eluting with 27% acetone/hexanes. Yield: 2.0 g, m.p. =96°–98° C.; MS (FAB) m/e M+K=830.

EXAMPLE 1c

Formula II: $R^8$=—OSO$_2$F; $R^9$=H

The title compound was prepared from the title compound of Example 1 b and fluorosulfonyl anhydride according to the procedure described in Example 1a. MS (FAB) m/e M+K=912.

EXAMPLE 2

Formula II: $R^8$=H; $R^9$=—OSO$_2$CF$_3$

The title compound was prepared from ascomycin and trifluoromethanesulfonyl anhydride according to the procedure described in Example 1a. MS (FAB) m/e M+K=962.

EXAMPLE 3

Formula II: $R^8$=—OSO$_2$CF$_3$; $R^9$=H

The title compound was prepared from the title compound of Example 1 b and trifluoromethanesulfonyl anhydride according to the procedure described in Example 1a. MS (FAB) m/e M+K=962.

EXAMPLE 4

Formula II:
$R^8$=—S—[2'—(1—methyl—tetrazolyl)]; $R^9$=H

Trifluoromethanesulfonyl anhydride (0.4 g) in dichloromethane (1 mL) was added into a stirred solution of ascomycin (0.8 g) and diisopropylethylamine (0.5 g) in dichloromethane at 0° C. After being stirred at 0° C. for 15 minutes, 5-mercapto-1-methyl-tetrazole (0.23 g) was added and the reaction mixture was stirred at room temperature for 24 hours. The product was purified by silica gel chromatography (70 g) eluting with 10% acetone-hexanes. Yield: 0.5 g; m.p. =106°–110° C.; MS (FAB) m/e M+NH$_4$ =907.

EXAMPLE 5

Formula II: $R^8$=H;
$R^9$=—S—[2'—(1—methyl—imidazolyl)]

1-Methyl-2-mercapto-imidazole (0.46 g) was added into a solution of the title compound of Example 1a (2 g) and diisopropylethylamine (0.4 mL) in dichloromethane (10 mL) at 0° C. After being stirred at room temperature overnight, the reaction was purified by silica gel chromatography (250 g) eluting with 40% acetone-hexanes. Yield: 1.4 g; m.p. =92°–96° C.; MS (FAB) m/e M+H=888.

EXAMPLE 6

Formula II: $R^8$=H;
$R^9$=—S(O)—[2'(1—methyl—imidazolyl)]

m-Chloroperbenzoic acid (0.2 g, 50% pure) was added into a stirred mixture of the title compound of Example 5 (0.15 g) and cesium carbonate (0.16 g) in dichloromethane (1.5 mL) and stirred at room temperature overnight. The product was purified by silica gel chromatography (3 g) eluting with 70% acetone in hexanes. Yield: 0.093 g; MS (FAB) m/e M+K=942.

EXAMPLE 7

Formula II: $R^8$=H;
$R^9$=—S—[3'—(1'H—1,2,4,—triazolyl)]

The title compound was prepared from the title compound of Example 2 and 1H-1,2,4-triazole-3-thiol in the presence of diisopropylethylamine according to the procedure described in Example 5. M.p. =98°–100° C.; MS (FAB) m/e M+H=875.

EXAMPLE 8

Formula II: $R^8$=H; $R^9$=—S—[2'—pyrimidinyl]

The title compound was prepared from the title compound of Example 1a and 2-mercaptopyrimidine in the presence of diisopropylethylamine according to the procedure described in Example 5. M.p. =118°–126° C.; MS (FAB) m/e M+NH$_4$=903.

EXAMPLE 9

Formula II: $R^8$=H;
$R^9$=—S(O)$_2$—[2'—(1'—methyl—imidazolyl)]

The title compound is prepared from the title compound of Example 6, N-methylmorpholine-N-oxide and ruthenium tetraoxide.

EXAMPLE 10

Formula II: $R^8$=H;
$R^9$=—S—[2'—(4'—methylpyrimidinyl)]

The title compound is prepared from the title compound of Example 1a and 2-mercapto-4-methylpyrimidine in the presence of diisopropylethylamine according to the procedure described in Example 5.

EXAMPLE 11

Formula II:
$R^8$=—S—[2'—(1'—methyl—tetrazolyl)]; $R^9$=—H

The title compound is prepared from the title compound of Example 1c and 1-methyl-2-mercapto-tetrazole in the presence of diisopropylethylamine according to the procedure described in Example 5.

EXAMPLE 12

Formula II:
$R^8$=—S—[2'—(1'—methyl—imidazolyl)]; $R^9$=—H

The title compound is prepared from the title compound of Example 1 c and 1-methyl-2-mercapto-imidazole in the presence of diisopropylethylamine according to the procedure described in Example 5.

EXAMPLE 13

Formula II:
$R^8$=—S—[3'—(1'—H—1,2,4—triazolyl)]; $R^9$=—H

The title compound is prepared from the title compound of Example 1 c and 1H-1,2,4-triazole-3-thiol in the presence of diisopropylethylamine according to the procedure described in Example 5.

EXAMPLE 14

In Vivo Assay of Biological Activity

The immunosuppressant activity of the compounds of the present invention was determined using the human mixed lymphocyte reaction (MLR) assay described by Kino, T. et al. in *Transplantation Proceedings*, XIX(5):36–39, Suppl. 6 (1987). The results of the assay, shown below in Table 1, demonstrate that the compounds tested are effective immunomodulators at sub-micromolar concentrations.

TABLE I

| Example # | IC$_{50}$ (10 × 10$^{-9}$M) |
|---|---|
| 4 | 1.1 |
| 5 | 1.6 |
| 6 | 3.5 |
| 8 | 2.5 |

It is understood that the foregoing detailed description and accompanying examples are merely illustrative and are not to be taken as limitations upon the scope of the invention, which is defined solely by the appended claims and equivalents thereof. Variations and modifications of the disclosed embodiments will be apparent to those skilled in the art. Such variations and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula:

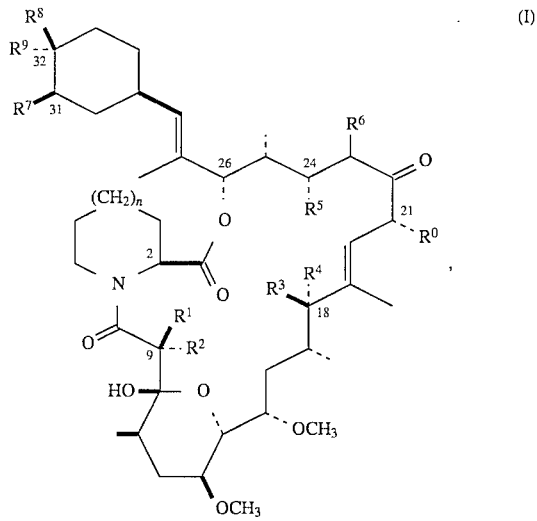

or a pharmaceutically acceptable salt, ester or amide thereof wherein the ester is selected from C1-to-C6 -alkyl esters, C5-to-C7 cycloalkyl esters, arylalky esters and esters resulting from reaction of an alcohol moiety in the compound of formula I with a C1-to-C6-alkyl carboxylic acid, a C1-to-C6-alkyl dicarboxylic acid or an arylcarboxylic acid and wherein the amide results from reaction of a carboxylic acid moiety in the compound of formula I with NH$_3$, NH$_2$(C1-to-C3-alkyl), NH(C1-to-C2 alkyl)$_2$ or a 5- or 6- membered ring heterocycle containing one nitrogen atom, wherein:

n is an integer selected from the group consisting of zero and one;

$R^0$ is selected from the group consisting of hydrogen, methyl, ethyl, allyl, propyl, 2-hydroxyethyl, cyclopropylmethyl, 2-oxopropyl and 2-ethanal;

$R^1$ and $R^2$ are independently selected from the group consisting of hydrogen and hydroxy, provided that at least one of $R^1$ and $R^2$ is hydrogen; or, taken together, $R^1$ and $R^2$ are oxo;

$R^3$ and $R^4$ are independently selected from the group consisting of hydrogen, halogen, and hydroxy, provided that at least one of $R^3$ and $R^4$ is hydrogen; or, taken together, $R^3$ and $R^4$ are oxo;

$R^5$ is selected from the group consisting of (a) hydrogen, (b) hydroxy and c) hydroxy protected by a hydroxy-protecting group selected from methylthiomethyl, dimethylthexylsilyl, tris(C1–C10-alkyl)silyl, C1–C10-alkyldiarylsilyl, triarylsilyl, tri(aryl-C1–C10-alkyl)silyl, C1–C10-alkyl-C(O)—, aryl—C(O)—, C1–C10-alkoxycarbonyl, —S(O)$_2$—(C1–C10-alkyl), and —S(O)$_2$—(aryl);

$R^6$ is hydrogen; or, taken together, $R^5$ and $R^6$ form a C-23/C-24 bond;

R[7] is selected from the group consisting of (a) hydroxy, (b) methoxy and (c) hydroxy protected by a hydroxy-protecting group independently as defined above; and R[8] are selected such that one of R[8] and R[9] is hydrogen and the other is —S(O)$_s$—Het, where s is an integer selected from the group consisting of zero, one and two;

wherein at each occurrence the term Het or heterocyclic is independently selected from the group consisting of pyrrolyl, pyrazolyl, cytosinyl, thiocytosinyl, imidazolyl, pyridyl, pyrazinyl, pyrimidinyl pyridazinyl, xanthenyl, xanthonyl, xanthopterinyl, oxazoyl, thiouracilyl, isoxazolyl, indolyl, quinolinyl, uracilyl urazolyl, uricyl, triazolyl, tetrazolyl, thiazolyl, isothiazolyl, isoquinolinyl, thyminyl, benzimidazolyl, benzothiazolyl, benzoxazolyl, furyl, thienyl and benzothienyl wherein any carbon or heteroatom with suitable valence may bear a substituent independently selected at each occurrence from the group consisting of halogen, hydroxy, —COOH, —CN, —CHO, —NO$_2$, —N$_3$, —(C1–C6-alkyl), —(C2–C6-alkenyl), —(C2–C6-alkynyl), mono-, di- tri-, or perhalogenated —C1–C6-alkyl, —(CH2)$_m$N(C1–C6-alkyl)$_2$ where m is zero to six, —S(O)$_s$(C1–C6-alkyl) where s is zero to two, —C(O)NH(C1–C6-alkyl), —(CH$_2$)$_m$O(C1–C6-alkyl) wherein m is zero to six, —(CH$_2$)$_m$OC(O)(C1–C6-alkyl) wherein m is zero to six, —(CH$_2$)$_m$C(O)O(C1–C6-alkyl) wherein m is zero to six, —S(O)$_2$N(C1–C6-alkyl)$_2$—C≡C—Si(CH$_3$)$_3$,—C1–C6-alkoxy, —OC(O)(C1–C6-alkyl), guanidino, unsubstituted aryl, and unsubstituted Het.

and at each occurrence the term aryl is independently selected from the group consisting of phenyl, 1-naphthyl, 2-naphthyl, fluorenyl, (1,2)-dihydronaphthyl, (1,2,3,4)-tetrahydronaphthyl and indenyl wherein the aryl group is unsubstituted or substituted with one, two or three substituents independently selected from halogen, hydroxy, —COOH, —CN, —CHO, —NO$_2$, —N$_3$, —(C1–C6-alkyl),—(C2–C6-alkenyl), —(C2–C6-alkynyl), mono-, di-tri-, or perhalogenated —C1–C6-alkyl, —(CH$_2$)$_m$N(C1–C6-alkyl)$_2$ where m is zero to six, —S(O)$_s$(C1–C6-alkyl) where s is zero to two, —C(O)NH(C1–C6-alkyl), —(CH$_2$)$_m$O(C1–C6-alkyl) wherein m is zero to six, —(CH$_2$)$_m$OC(O)(C1–C6-alkyl) wherein m is zero to six, —(CH$_2$)$_m$C(O)O(C1–C6-alkyl) wherein m is zero to six, —S(O)$_2$N(C1–C6-alkyl)$_2$, —C≡C—Si(CH$_3$)$_3$, —C1–C6-alkoxy, —OC(O)(C1 –C6-alkyl), guanidino, unsubstituted aryl, and unsubstituted Het.

2. A compound according to claim 1 wherein the integer n is one.

3. A compound according to claim 1 wherein R[0] is selected from the group consisting of ethyl, allyl and propyl.

4. A compound according to claim 1 wherein R[1] and R[2], taken together, are oxo.

5. A compound according to claim 1 wherein R[3] and R[4] are independently selected from the group consisting of hydrogen and hydroxy, provided that at least one of R[3] and R[4] is hydrogen.

6. A compound according to claim 1 wherein R[5] is selected from the group consisting of hydrogen and hydroxy.

7. A compound according to claim 6 wherein R[5] is hydroxy.

8. A compound according to claim 1 wherein R[7] is methoxy.

9. A compound according to claim 1 wherein R[8] is —S(O)$_s$—Het wherein s and Het are as defined therein.

10. A compound according to claim 1 wherein Het is selected from the group consisting of pyrrolyl, pyrazolyl, imidazolyl, pyridyl, pyrazinyl, pyrimidinyl, indolyl, triazolyl and tetrazolyl.

11. A compound according to claim 1 having the formula:

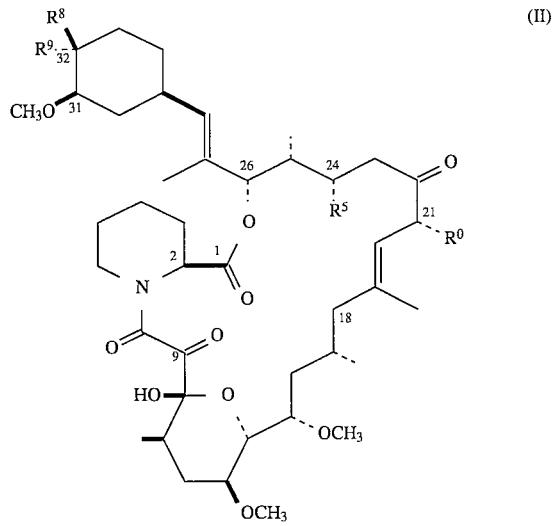

where R[0], R[5], R[8] and R[9] are as defined therein.

12. A compound according to claim 11 wherein R[0] is selected from the group consisting of ethyl, allyl and propyl.

13. A compound according to claim 11 wherein R[5] is selected from the group consisting of hydrogen and hydroxy.

14. A compound according to claim 13 wherein R[5] is hydroxy.

15. A compound according to claim 11 wherein R[8] is —S(O)$_s$—Het wherein s and Het are as defined therein.

16. A compound according to claim 11 wherein Het is selected from the group consisting of pyrrolyl, pyrazolyl, imidazolyl, pyridyl, pyrazinyl, pyrimidinyl, indolyl, triazolyl and tetrazolyl.

17. The compound according to claim 1 wherein R[0] is ethyl, R[1] and R[2] taken together are oxo, R[3] is hydrogen, R[4] is hydrogen, R[5] is hydroxy, R[6] is hydrogen, R[7] is methoxy and (i) R[8] is hydrogen and R[9] is —S-(2'-(1'-methyl-imidazolyl)), —S(O)(2'-(1'-methyl-imidazolyl)), —S-(3'-(1'-H-1,2,4-triazolyl)), —S—(2'-pyrimidinyl), —S(O)$_2$-(2'-(1'-methyl-imidazolyl)) or —S-(2'-(4'-methylpyrimidinyl)) or (ii) R[9] is hydrogen and R[8] is —S-(2'-(1'-methyltetrazolyl)), —S-(2'-(1'-methylimidazolyl)) or —S-(3'-(1'-H-1,2,4-triazolyl)).

* * * * *

UNITED STATES PATENT AND TRADEMARK OFFICE
CERTIFICATE OF CORRECTION

PATENT NO. : 5,561,137  
DATED : October 1, 1996  
INVENTOR(S) : Y. S. Or, et. Al.

Page 1 of 3

It is certified that error appears in the above-indentified patent and that said Letters Patent is hereby corrected as shown below:

In the abstract, please correct the structural formula therein to look like this:
Also column 4, lines 6-25

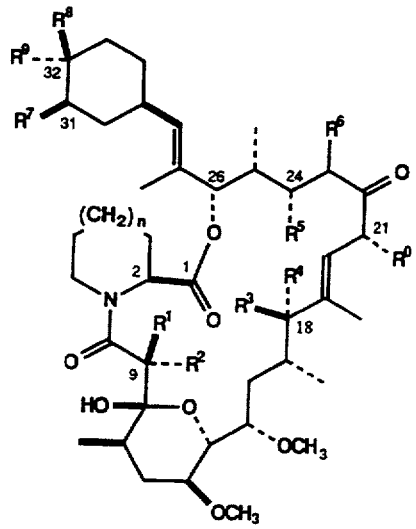

UNITED STATES PATENT AND TRADEMARK OFFICE
CERTIFICATE OF CORRECTION

PATENT NO. : 5,561,137
DATED : October 1, 1996
INVENTOR(S) : Y. S. Or, et. Al.

Page 2 of 3

It is certified that error appears in the above-indentified patent and that said Letters Patent is hereby corrected as shown below:

Column 20, lines 14-33, please correct the structural formula therein to look like this:

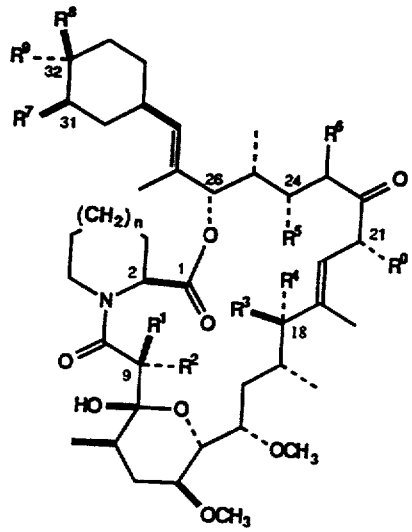

(I)

UNITED STATES PATENT AND TRADEMARK OFFICE
CERTIFICATE OF CORRECTION

PATENT NO. : 5,561,137
DATED : October 1, 1996
INVENTOR(S) : Y. S. Or, et. Al.

It is certified that error appears in the above-indentified patent and that said Letters Patent is hereby corrected as shown below:

Column 20, line 36, change "arylalky" to --arylalkyl--.

Column 21, line 4, change "$R^8$ are" to --$R^8$ and $R^9$ are--.

Column 21, line 41, change "-$(CH_2)_m$" to -- -$(CH2)_m$--.

Signed and Sealed this

Eighth Day of April, 1997

*Attest:*

BRUCE LEHMAN

*Attesting Officer*   Commissioner of Patents and Trademarks